United States Patent
De Pablos García et al.

(10) Patent No.: US 11,612,469 B2
(45) Date of Patent: Mar. 28, 2023

(54) DEVICE FOR MEASURING DENTAL PARAMETERS

(71) Applicants: TECH XIKA PTT, S.L., Lleida (ES); IDIS, S.L., Madrid (ES)

(72) Inventors: David De Pablos García, Madrid (ES); Alfonso Fernández Pulido, Madrid (ES)

(73) Assignees: TECH XIKA PTT, S.L., Lleida (ES); IDIS, S.L., Madrid (ES)

(*) Notice: Subject to any disclaimer, the term of this patent is extended or adjusted under 35 U.S.C. 154(b) by 247 days.

(21) Appl. No.: 17/043,422

(22) PCT Filed: Apr. 5, 2018

(86) PCT No.: PCT/ES2018/070297
§ 371 (c)(1),
(2) Date: Sep. 29, 2020

(87) PCT Pub. No.: WO2019/193216
PCT Pub. Date: Oct. 10, 2019

(65) Prior Publication Data
US 2021/0145558 A1      May 20, 2021

(51) Int. Cl.
*A61C 19/05* (2006.01)
*A61B 1/06* (2006.01)
*A61B 1/24* (2006.01)

(52) U.S. Cl.
CPC ............ *A61C 19/05* (2013.01); *A61B 1/0684* (2013.01); *A61B 1/24* (2013.01)

(58) Field of Classification Search
CPC ..... A61C 19/05; A61C 19/052; A61C 9/0053; A61C 19/04; A61C 19/004;
(Continued)

(56) References Cited

U.S. PATENT DOCUMENTS

| 4,324,547 A | 4/1982 | Arcan et al. |
| 4,575,805 A | 3/1986 | Moermann et al. |

(Continued)

FOREIGN PATENT DOCUMENTS

| EP | 0216899 A | 4/1987 |
| JP | 2004033465 A | 2/2004 |

(Continued)

OTHER PUBLICATIONS https://byjus.com/maths/parallelepiped/ (Year: 2022).*
ISR-WO for parent application PCT/EP2018/070297 (WO2019/193216) dated Jan. 4, 2019.

*Primary Examiner* — Edward Moran
*Assistant Examiner* — Luis M Ruiz Martin
(74) *Attorney, Agent, or Firm* — Vorys, Sater, Seymour and Pease LLP (57) ABSTRACT

The invention relates to a device for measuring dental parameters, more specifically for measuring alignment, bite pressure and dental occlusion in a subject, the device being formed from a main body containing a light source and at least one image-recording element linked with an image processor disposed in a control unit. The device includes a cartridge that is inserted automatically into the main body, the cartridge including a support for a plate of soft material for imprinting the bite of a subject. The main body also contains traction elements for the plate support and, optionally, for the at least one image-recording element, as well as a display screen disposed on the outside of said main body.

12 Claims, 6 Drawing Sheets

(58) Field of Classification Search
CPC ... A61C 19/0093; A61C 19/08; A61B 1/0684; A61B 1/07; A61B 1/24; A61B 6/14; A61B 6/145
See application file for complete search history.

(56) References Cited

U.S. PATENT DOCUMENTS

| | | |
|---|---|---|
| 8,989,567 B1 | 3/2015 | Fernández Pulido et al. |
| 2002/0058229 A1 | 5/2002 | Sugimoto |
| 2005/0153257 A1 | 7/2005 | Durbin et al. |
| 2017/0181815 A1* | 6/2017 | Pulido .................. A61C 9/0053 |

FOREIGN PATENT DOCUMENTS

| | | | | |
|---|---|---|---|---|
| KR | 101696377 B1 * | 1/2017 | | |
| WO | WO-2014083211 A1 * | 6/2014 | ......... | A61B 1/00172 |
| WO | 2019193216 A1 | 10/2019 | | |

* cited by examiner

DEVICE FOR MEASURING DENTAL PARAMETERS

BACKGROUND OF THE DISCLOSURE

The present invention relates to a device for measuring dental parameters, more specifically a device for measuring alignment, bite pressure and dental occlusion in a subject. The invention also relates to the use of the device of the invention in the design of treatments for pathologies related to dental occlusion, bite imbalances or dental alignment.

The device of the invention thus allows, among other things, measuring dental alignment, for example for "brackets" treatment, enabling taking measurements of said dental alignment from time to time even by the subject treated with said treatment, since it is an easy-to-use device and provides data in a digital format to be incorporated into existing computerized treatment methods. Likewise, the device of the invention facilitates a diagnosis through pressure and bite occlusion in an easy and immediate way, with no need to use silicone molds, with the results being further digitized to apply to existing computerized treatment methods.

The alignment of teeth, and the way upper and lower teeth fit together during the bite, is generally known as dental occlusion. Thus, ideally, the upper teeth should snap or fit slightly over the lower teeth, and the points of the molars should snap into the grooves of the opposite molars. Upper teeth prevent the cheeks and lips from being bitten and the lower teeth protect the tongue. Occlusion may be due to a difference between the size of the upper and the lower jaws, or between the size of the jaw and the tooth. This causes dental crowding or abnormal bite patterns. The shape of the jaw or birth defects, such as cleft lip and palate, can also be reasons for defective dental occlusion. Among other causes, childhood habits such as thumb sucking, tongue thrusting, bottle or pacifier use beyond age 3 and prolonged use of a bottle, the presence of extra, impacted, lost or abnormally formed teeth, ill-fitting dental fillings, crowns, prosthesis, retainers, or braces, and misalignment of jaw fractures after severe injury or tumors of the mouth and jaw can be identified as reasons for defective dental occlusion. The most common consequences of defective dental occlusion are abnormal alignment of teeth, abnormal appearance of the face, difficulty or discomfort when chewing or biting, and difficulties in speech (rare), including babbling or mouth breathing (breathing through the mouth without closing the lips).

The aim of treatment is to correct the positioning of the teeth, allowing the teeth to be easier to clean, reducing the risk of tooth decay and periodontal diseases (gingivitis or periodontitis), and eliminating stress on the teeth, jaw and muscles. This lowers the risk of a tooth breaking and can reduce the symptoms of temporomandibular joint disorders. Typically, treatments include application of "brackets" (braces) or other appliances (Dean J A. Managing the developing occlusion. In: Dean J A, ed. McDonald and Avery's Dentistry for the Child and Adolescent. 10th ed. St. Louis, Mo.: Elsevier; 2016: 22; Tinanoff N. Malocclusion. In: Kliegman R M, Stanton B F, St Geme J W, Schor N F, eds. Nelson Textbook of Pediatrics. 20th ed. Philadelphia, Pa.: Elsevier; 2016: 309).

In order to carry out measurements focused on treatments, various appliances and sensors are known in the art which allow an occlusal analysis to be carried out in order to know the relationship between the teeth occlusal faces of both arches, among which must be a presence of enough cusp-fossa or cusp-marginal ridge contacts. For this reason, there is a need for methods or tools which allow occlusal alterations to be clinically detected and carry out an objective analysis of the occlusion. For this, in clinical practice, devices referred to as occlusal indicators are used, with the objective of locating contacts and defining the intensity with which each one of them occurs (Dr. Marta Munoz Carcavilla, Associate Professor of the Master of Periodontology and Implants. University of Seville, "Importancia de la valoración digitalizada de los contactos oclusales" (Importance of the digitalized assessment of occlusal contacts), in Gaceta Dental Magazine September 2011).

Some of the occlusal indicators, such as articulating paper, are common tools in the diagnosis of occlusal situation, occlusal adjustment or placement of prostheses. There is no information and no publications proposing protocols for the use of occlusal indicators (Lawrence J. How occlusal forces change in implants patients: A clinical research report. JADA 1995; 126: 1130-1132). Even so, clinicians integrate these diagnostic methods in their daily clinics, assuming knowledge of their correct use.

There are two categories of occlusal indicators: dynamic and static. Static occlusal indicators are capable of identifying the location or position of different contact points; examples include, but are not limited to, different types of articulating paper, occlusion waxes, and aluminum strips. Traditionally, this type of indicator has been the most used in dental practice. On the other hand, dynamic occlusal indicators are capable of discriminating, over time, the sequence of appearance of different points of contact and their intensity in an objective way; for example, computerized occlusal analysis systems, such as T-Scan system and Foto-oclusión.

Articulating paper is the most common occlusal indicator used in the dental practice. They are thin sheets of tinted paper and are available in different thicknesses. By using them after patient occlusion, occlusal contacts can be registered. Because they are too thin and flexible, and the presence of saliva can affect their results, their use can exhibit the appearance of a large number of pseudo-contacts. Articulating paper can be made in different materials and colors, producing tinted marks in the area of occlusal contact. Each mark is assumed to represent a contact and the transfer is exact. In the dental practice it is accepted that the characteristics of the occlusal marks may be associated with the occlusal force created; thus, large and dark-colored marks would indicate an occlusal pressure stronger than that of light-colored and smaller ones. However, Kerstein (Kerstein R B. T-Scan III Applications in mixed arch and complete arch, implant-supported prosthodontics. Dent Impl 2008; July (19), 7: 49-53.9) proved there is little relationship between marks of articulating paper and the intensity of the force produced; it seems that the more intense forces tend to leave less of an ink mark on the tooth surface, thus being able to represent the same force intensity with marks of different sizes and shapes. Likewise, one of the problems of articulating paper is its surface (material) and thickness: a thick and rough articulating paper can create friction and resistance in occlusal contact, while a thin and smooth one does not engage on the irregularities of enamel or ceramics, making it difficult in both cases to obtain registrations. Thus, one of the main disadvantages of articulating paper is that the results obtained do not constitute a reliable or exact registration, since they entail a subjective interpretation by the clinician who decides which contacts present greater strength based on color and size, with the possibility of there being clear differences between the criteria of one clinician and another (Carey. Determining a relationship between applied occlusal load and articulating paper mark area. The Open Dent J 2007; (1); 1-7).

Another type of static device used includes silk strips and aluminum strips. Some authors have established that silk strips are the best occlusal indicator, claiming that this type of material presents ideal characteristics due to its texture and it not producing pseudo-contacts; however, it has been observed that it could lose its qualities when totally dry or in the presence of an environment with saliva. This fact makes it necessary for them to be previously impregnated with petroleum jelly (Saraçoglu A, Özpinar B. In vivo and in vitro evaluation of occlusal indicator sensitivity. J Prosthet Dent 2002; 88: 522-6).

The use of other types of materials, such as silicone registers, has been studied in works such as that of Ziebert and Donegan (Ziebert G J & Donegan. Tooth contacts and stability before and after occlusal adjustment. J Prosth Dent 1979; 42 (3): 276-281), where perforations that occurred in the silicone before and after occlusal adjustment were analyzed. They made two registrations in each model in maximum intercuspation and in retrusion. The perforations indicated produced contact points. They compared the coincidence between these contacts in study models and intraorally, observing that the degree of coincidence and accuracy was lower than expected. Inter-operator reproducibility was checked by repeating each registration until two identical records were obtained; it is not clear how the decision was made when two records were equal, so inter-operator reliability could not be verified.

The other group of occlusal indicators, the dynamic ones, is made up of those devices that evaluate the sequence and intensity over time of occlusal contacts; these are Foto-oclusión and T-Scan systems. The Foto-oclusión system (Saraçoglu A, Özpinar B. In vivo and in vitro evaluation of occlusal indicator sensitivity. J Prosthet Dent 2002; 88: 522-6) is based on a photoplastic film that is placed on the occlusal surface of teeth, allowing a dynamic analysis of the occlusal relationship. It consists of a thin sheet (0.1 mm) made of transparent plastic. Depending on the penetration of teeth into the sheet while the patient is being occluded for 10-20 seconds, variations in the color of the sheet occur, which are evaluated with polarized light. Foto-oclusión was developed with the aim of registering and measuring occlusal contacts based on photoelasticity, an optical technique to measure stress in materials. One of the disadvantages of this technique, according to some authors, is the difficulty of using it.

In 1987, Tekscan (South Boston, Mass.) developed the T-Scan Occlusal Analysis System, digital technology used to learn the intensity of occlusal forces of each tooth during chewing. In this regard, see for example EP0216899, "A contact sensor for measuring dental occlusion", where a contact sensor is described including a group of parallel electrodes grouped in rows, another group of parallel electrodes grouped in columns and a resistive layer sensitive to pressure between both groups of electrodes.

The T-Scan III system is the latest marketed version of software allowing digitizing the location and time of inter-cuspid contacts. It measures relative occlusal force and the time spent on a complete dental closure. It also allows the sequential assessment of contacts both in maximum intercuspation and in excursive movements (laterality and protrusive). With this system it is possible to register multiple other types of information regarding loads, load sequences and time spent in loading during different mandibular movements. The digitization of occlusal points is carried out by a U-shaped or fork-shaped sensor having a thickness of 60 μm (FIG. 3). The interior of this is formed by an X-Y coordinate system with 1,500 sensitive receptor points made with a conductive ink, subjected to elastic deformation. The information on the forces produced by the occlusion is received by these receivers and transferred to a computer, where it is digitized, transforming data obtained into graphics.

There are numerous articles in the literature about the clinical application of T-Scan; Hsu et al (Hsu M, Palla S, Gallo L M. Sensitivity and reliability of the T-scan system for occlusal analysis. J Craniomandib Disord 1992; 6: 17-23) observed the sensitivity and reproducibility of the T-Scan system, concluding that the sensors did not present the same sensitivity on the surface and registered less contact than occlusal paper. With quantitative analysis devices as well as with the T-Scan system, we accurately registered the intensity of contact over time; however, this system does not locate the position of the contact point since the sensor is based on standardized estimates of dental positions.

Studies published such as that by Saracoglu et al (Saraçoglu A, Özpinar B. In vivo and in vitro evaluation of occlusal indicator sensitivity. J Prosthet Dent 2002; 88: 522-6), in which they compared sensitivity and coincidence between various qualitative and quantitative devices, conclude that there are differences in the number of contacts between the three systems analyzed, finding a lower sensitivity in the T-Scan compared to other systems; the sensitivity of the T-Scan can be adversely affected when the sensors are used multiple times, while the articulating paper is recommended for a single use. In other systems, it was observed that the number of registered contacts increased when there was no saliva on occlusal surfaces, whereas this did not seem to affect the T-Scan system. In Baba's article (Baba K. Reliability, validity, and utility of various occlusal measurement methods and techniques, Kazuyoshi Baba, J Prosthet Dent 200; 83: 83-89), 37 articles were reviewed in which methods and techniques were assessed regarding the reproducibility and usefulness of instruments that assessed occlusion, including both static and dynamic devices. It was observed how electromyographic registrations could measure activation of jaw muscles and their position, although the cost-benefit relationship of this type of device is not clear. Finally, the authors concluded that none of the instruments reviewed in the different publications presented results that validated their use and reproducibility.

SUMMARY OF THE INVENTION

The present invention solves the disadvantages of the aforementioned sensors, providing a device for measuring dental parameters that combines the advantages of static sensors and dynamic sensors.

To this end, a device for measuring dental parameters, more specifically for measuring alignment, bite pressure and dental occlusion in a subject, is formed on the basis of a main body inside which a light source is housed, and at least one image-recording element associated with an image processor is arranged in a control unit. The device also includes a cartridge that is automatically inserted into the main body, the cartridge including a plate support, such that the plate is made of a soft material, for the impression of a subject's bite. The main body also includes, on its inner part, traction elements for the plate support and optionally for the at least one image-recording element, as well as a display screen disposed on the outside of said main body.

BRIEF DESCRIPTION OF THE DRAWINGS

The invention is described in more detail below based on an example embodiment thereof and referring to the attached figures, in which.

DETAILED DESCRIPTION

Figure 1:
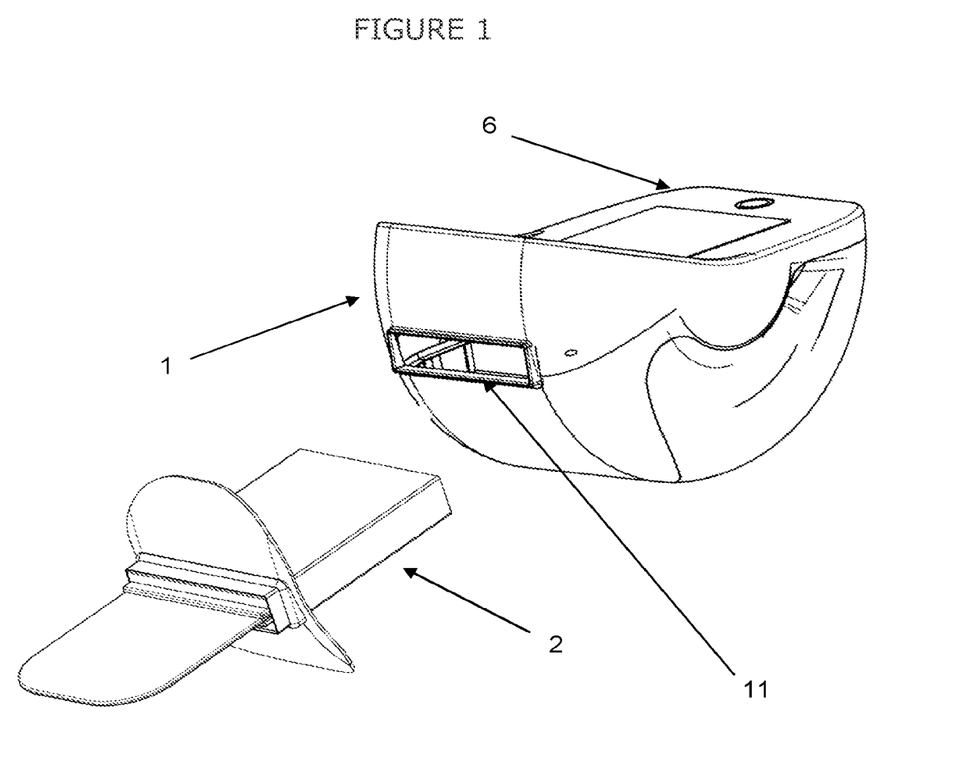
FIG. 1 is a schematic representation of an example of a device of the invention in a perspective view.
Figure 4:
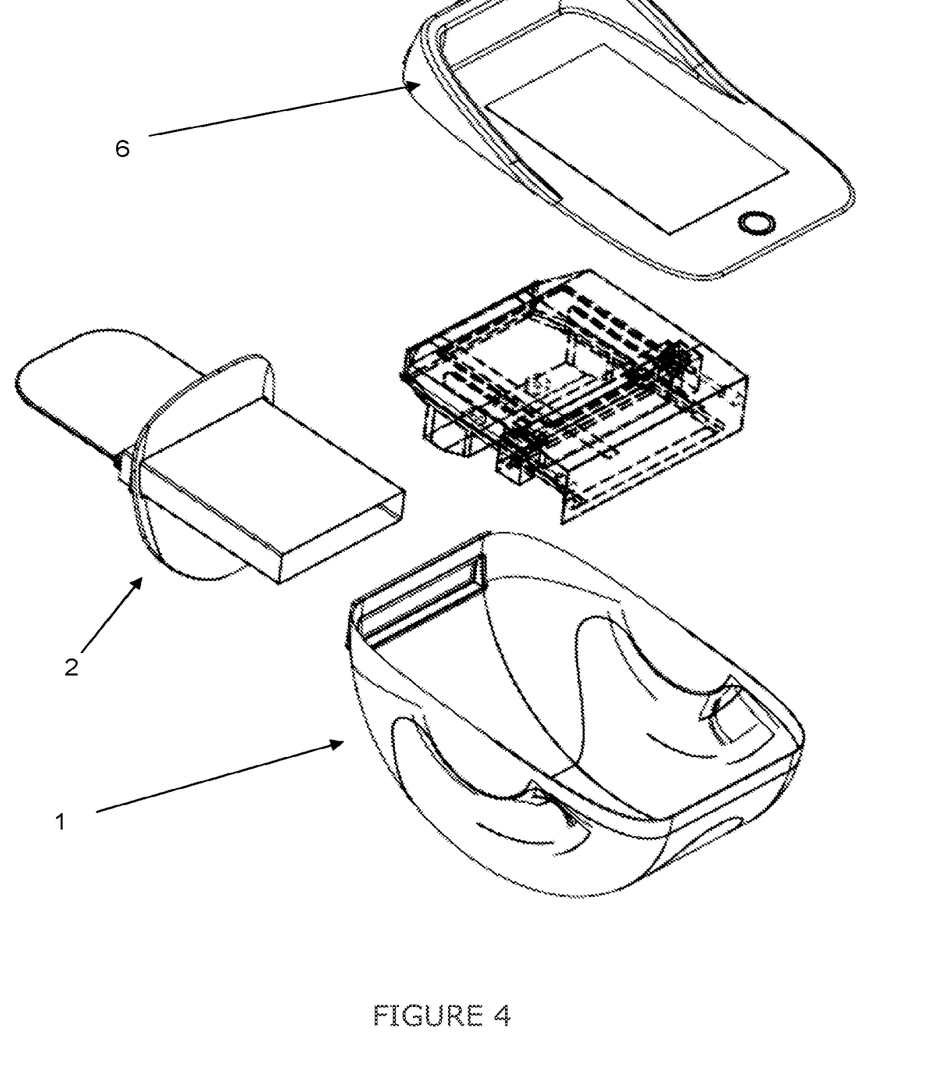
FIG. 4 is an exploded view of the device of FIG. 1.

As can be seen in FIGS. 1 and 4, the device for measuring dental parameters essentially consists of a main body (1) and a cartridge (2).

Figure 2:
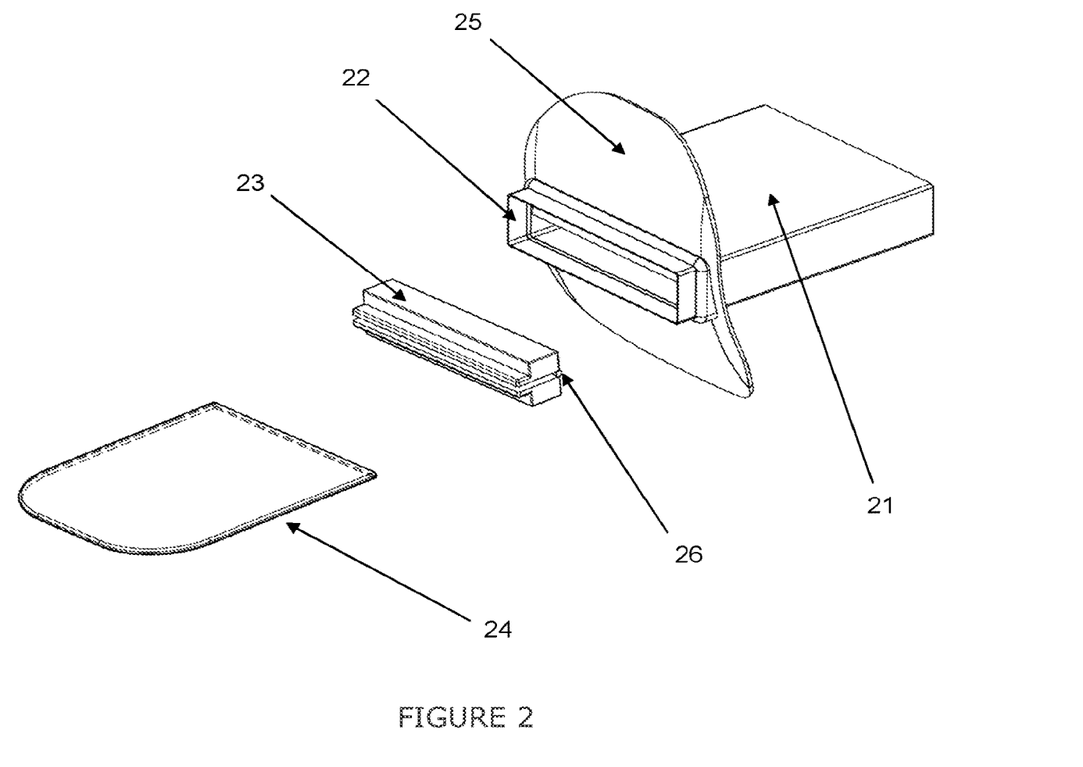
FIG. 2 is an exploded schematic representation of the cartridge of the device of FIG. 1.

Referring first to the cartridge (2), which is shown in an exploded view in FIG. 2, it is made from a hollow parallelepiped body (21) which is open at its ends. At a first proximal end (22) thereof, understanding that the proximal end is the end that, in use, is closest to the patient's mouth (see FIG. 6), the hollow body (21) includes a frame (23) constituting the boundary and support of a plate (24) on which a soft sheet material is disposed, such as a sheet wax.

Figure 3:
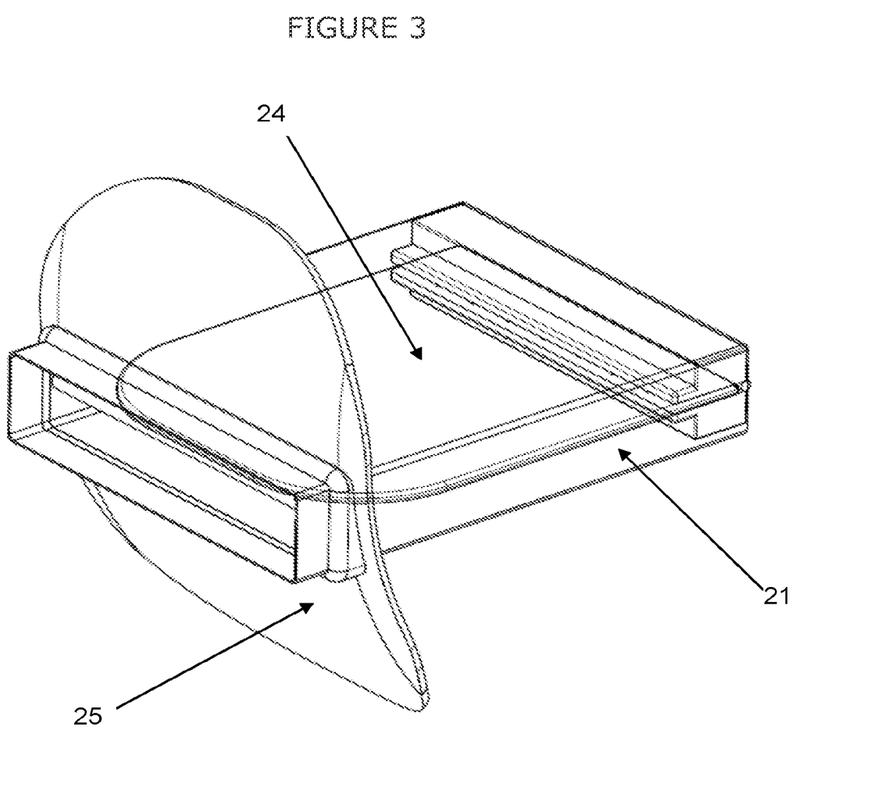
FIG. 3 is a schematic representation of the cartridge of the device of FIG. 1 in a state with the plate inside.

At the distal end of the frame (23) a ferromagnetic metallic element (26) is arranged, such as a ferromagnetic metallic rod, which, in use, as will be later described in detail, cooperates with an electromagnet correspondingly arranged in the main body (1) to activate traction elements of the frame (23), such that the frame (23) carrying the plate (24) automatically enters or leaves the main body (1). In this regard, see for example FIGS. 3 and 6. For this, cartridge (2) includes guide rails (not shown) on its inner side walls.

Material from which the cartridge is made is a transparent material, for example a transparent plastic, preferably a transparent plastic material resistant to sterilization, for example in an autoclave. In one embodiment of the invention the cartridge is disposable and is replaced with every use.

Optionally, the cartridge (2) includes a vertical separator element (25) constituting a hygienic barrier between the main body (1) and the subject.

Figure 6:
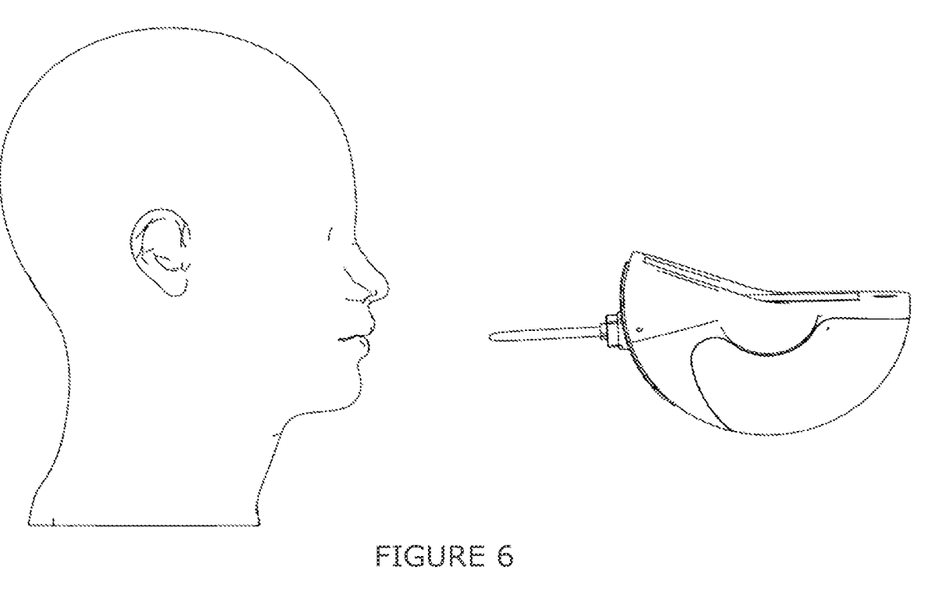
FIG. 6 is a schematic view of the device in an assembled state and ready for use.

Referring again to FIG. 1, the main body (1) has a groove (11) for inserting the hollow body (21) into its proximal area, thus being arranged inside the main body (1) when the device is in use (FIG. 6).

Figure 5:
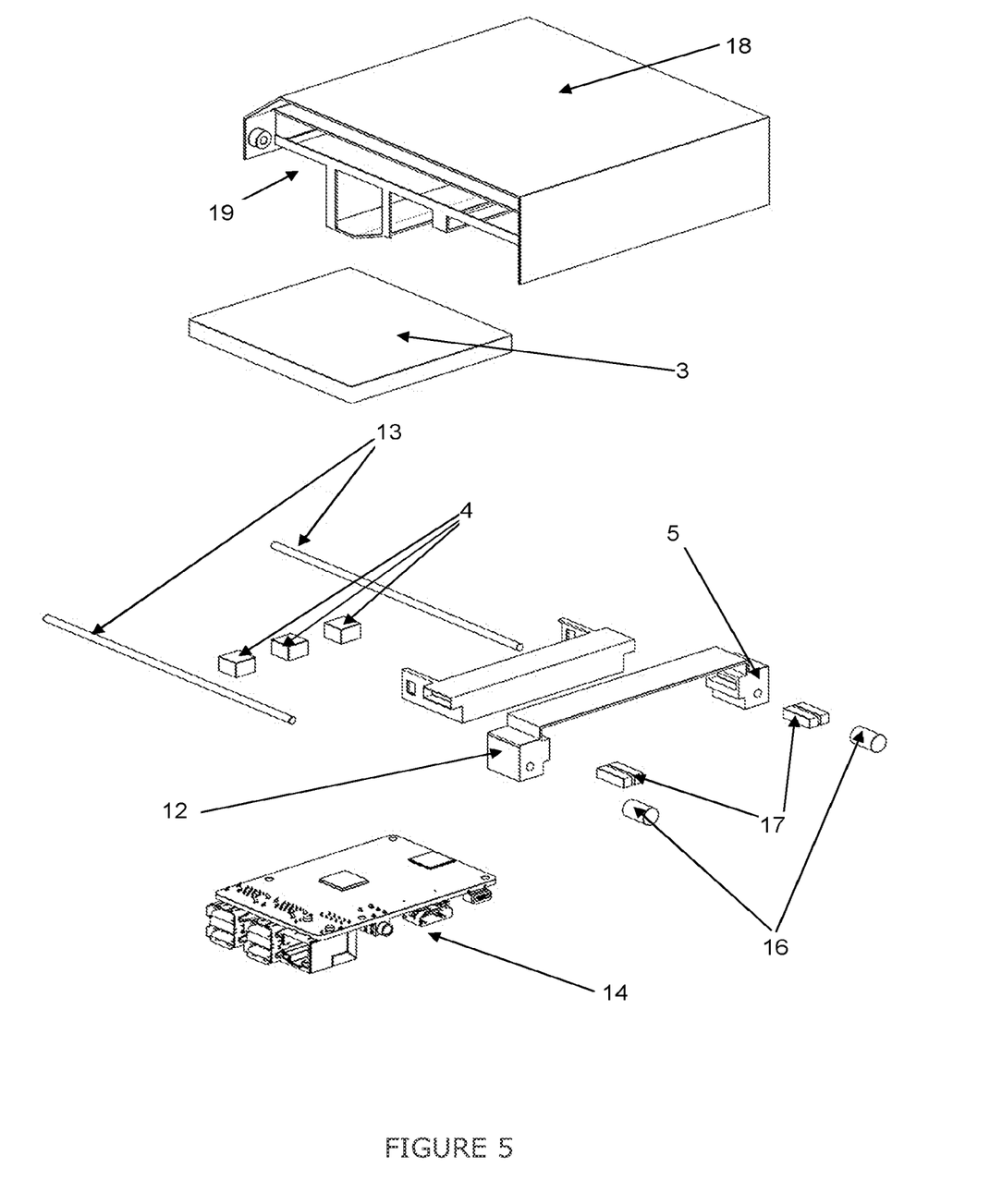
FIG. 5 is a detail view of the interior of the main body of the device of FIG. 1.

Referring now to FIG. 5, as mentioned above, the main body (1) houses a light source (3) in its inner part. Although not explicitly shown in FIG. 5, the light source (3) is made up of a grid pattern of lights covered by a white translucent plate, so that light passes through the translucent plate uniformly along its entire surface, similar to bedside tables commonly used for X-ray observation.

In one embodiment of the invention, the light source consists of a grid pattern of LEDs. In another embodiment of the invention, the light source is made up of a grid pattern of RGB LEDs, also called multicolor white LEDs. In this case, RGB LEDs can generate warm to cool white light as needed to optimize image capture by the image-recording element.

In said main body (1), facing the light source (3) and at a corresponding distance slightly greater than the height of the hollow body (21), at least one image-recording element (4) is arranged, for example at least a photographic camera. Although three of these cameras are shown in the figure, this embodiment is not limiting, such that any number of cameras may be appropriate for optimal image capture.

These image-recording elements (4) are suitably associated with an image processor arranged in a control unit (14) inside the main body (1).

Although the illustrated embodiment shows that the image-recording elements (4) are arranged in a fixed manner, optionally at least one of them can be moved in relation to width, length and/or height of the hollow body (21) by corresponding means, for example guide rails and associated motors, so that images can be recorded at different transverse positions, longitudinal positions, and/or at different heights. In this case, said control unit can also control said movements.

An electromagnet (12) correspondingly arranged in the main body (1) activates the traction element (5) of the frame (18)$_{[PT(1)]}$, for example a motor (5), so that the frame (23) carrying the plate (24) automatically enters or leaves main body (1). To guide this inlet/outlet, the main body has guide bars (13) on its side walls that slide through respective guide grooves (17) ending in corresponding stops (16) and cooperating with those arranged on side walls of hollow body (21). As shown in the figure, the frame (18) protects all the elements arranged inside the main body (1), this frame presenting an opening (19) for the entrance of the hollow body (21) of the cartridge (2).

Referring to plate (24) on which a soft sheet material, such as a sheet wax, is placed, the light reaching the image-recording elements (4) from the light source and passing through said soft material allows the device to obtain different points of transparency that match the dental occlusion.

Thus, when the subject introduces the plate (24) in his/her mouth and bites naturally on the soft material, the total perforation of this soft material defines a maximum transparency. This establishes within the image captured by the image-recording elements (4) of the plate (24), lit by light source (3), an area of occlusal contact. The area of occlusal contact entails the captured areas of semitransparency as an area of approach without contact between the dental pieces involved.

Since resolution of the camera may be insufficient for the entire plate, because a maximum resolution is desired, in an example embodiment several correlative photographs are taken, establishing a mosaic between them, and then all of them are joined by matching their edges to obtain an image with a greater resolution that is the sum of the previous ones. In order to achieve 5 microns in 10 cm of wax, there must be 20,000 pixels (1 pixel for every 5 microns), using 5,000 pixel cameras in this example that take four photographs.

In another example embodiment, for an 8×10 cm plate (24), a mosaic of 3×4 photographs is obtained.

In these examples, once the photographs have been assembled into a photograph with a maximum resolution of 5 microns, a computer program stored in the image processor arranged in a control unit inside the main body (1) analyzes the photograph using software and establishes that the most transparent points correspond to dental occlusion and colors them with a differentiating color, while coloring in another way, or not showing, the semi-transparent points due to proximity without contact between the teeth. The image processor can generate a downloadable data file for use with a dental work program, for example a dental alignment or occlusion analysis program. Likewise, the data file can be sent to any device of interest, wirelessly or through bluetooth.

Similarly, the image processor can display the analysis results on a display screen (6) arranged externally by closing the main body (1).

In another example, the image processor can generate a data file relating to the location of the colored contact points by defining their X, Y coordinates, and store them in a text file to establish a non-visual coordinate dental occlusion file.

In another example, using a soft material in the plate (24) of greater thickness, for example up to 8 mm thick, the device of the invention can be used with edentulous people to register the contact between gums in order to design dentures.

Similarly, in another example, a calibrated material is used in the plate (24), for example a material that requires a certain power or bite pressure to be pierced, for example 70 kg per cm$^2$, so that bite power can be quantified by means of the registered opacity or transparency. Thus, for example, for a material calibrated to the aforementioned 70 kg per cm$^2$, if the bite registered by the image capture elements (4) were to be half the thickness, the image processor would provide an intermediate color between the colors corresponding to opacity and total transparency, and it would be determined that the subject has maintained a bite pressure of 35 kg per cm$^2$. Furthermore, in this case, the device of the invention makes it possible to know if a subject generates an unbalanced bite power, for example if he/she presses more strongly on one area than on another, or stronger behind than in front or diagonally, which can result in a diagnosis of a pathology by the dentist.

The invention claimed is:

1. A device for measuring dental parameters of a subject, comprising:
    a main body and a cartridge of a transparent material;
    the main body comprising a light source, at least one image-recording element, an image processor, a control unit, an electromagnet, and a frame of the main body, wherein the light source, the at least one image-recording element, the image processor, the control unit, and the electromagnet are arranged inside the frame of the main body; and
    the cartridge comprising a hollow body opened at a proximal end and a distal end thereof, a frame of the cartridge supporting a plate at the distal end on which a soft sheet material, configured for obtaining a bite impression of the subject, is arranged, and a ferromagnetic metal element at the proximal end configured to cooperate with the electromagnet in the main body;
    wherein the electromagnet is configured to activate one or more traction elements of the frame of the main body, such that the frame of the cartridge carrying the plate automatically enters or leaves the main body.

2. The device for measuring dental parameters according to claim 1, wherein the light source consists of a grid pattern of lights covered by a white translucent plate.

3. The device for measuring dental parameters according to claim 1, wherein the light source consists of a grid pattern of LEDs covered by a white translucent plate.

4. The device for measuring dental parameters according to claim 3, wherein the LEDs are RGB LEDs.

5. The device for measuring dental parameters according to claim 1, wherein the cartridge is made of a plastic material resistant to sterilization.

6. The device for measuring dental parameters according to claim 1, wherein the cartridge includes a vertical separating element configured to create a hygienic barrier between the main body and the subject.

7. The device for measuring dental parameters according to claim 1, wherein the at least one image-recording elements are fixedly within the main body.

8. The device for measuring dental parameters according to claim 1, wherein at least one of the at least one image-recording elements is displaceably arranged on the main body, recording transversal, longitudinal and/or at different height images.

9. A method of using the device according to claim 1, comprising:
    obtaining an impression from the user on the soft sheet of material;
    inserting the plate and the soft sheet of material comprising the impression from the user into the main body; and
    passing light from the light source through the soft material arranged on the plate to the at least one image-recording element to record different points of transparency that define dental occlusion to measure the dental occlusion of the subject.

10. The method of claim 9, further comprising:
    analyzing, via the image processor, a recorded image such that transparency points that define a dental occlusion, semitransparency points that define a contactless approach zone, and non-contact opaque points are colored with differentiating colors; and
    generating a downloadable file.

11. The method of claim 10, further comprising:
    generating, via the image processor, a data file related to a location of the transparency points, semitransparency points, and non-contact points comprising:
    defining X and Y coordinates of the transparency points, semitransparency points, and non-contact points;
    storing the X and Y coordinates in a text file to generate a non-visual coordinate file; and
    generating a second downloadable file.

12. The method of claim 9, further comprising displaying collected data results on a display screen arranged within the main body.

* * * * *